(12) United States Patent
Ishii et al.

(10) Patent No.: US 6,768,030 B2
(45) Date of Patent: Jul. 27, 2004

(54) PROCESS FOR PRODUCING ORGANIC PEROXIDES

(75) Inventors: Yasutaka Ishii, Takatsuki (JP); Tatsuya Nakano, Himeji (JP); Atsuo Tatsumi, Himeji (JP)

(73) Assignee: Daicel Corporation Industries, Ltd., Osaka (JP)

( * ) Notice: Subject to any disclaimer, the term of this patent is extended or adjusted under 35 U.S.C. 154(b) by 0 days.

(21) Appl. No.: 10/416,579

(22) PCT Filed: Nov. 8, 2001

(86) PCT No.: PCT/JP01/09768

§ 371 (c)(1),
(2), (4) Date: May 13, 2003

(87) PCT Pub. No.: WO02/38538

PCT Pub. Date: May 16, 2002

(65) Prior Publication Data

US 2004/0039215 A1 Feb. 26, 2004

(30) Foreign Application Priority Data

Nov. 13, 2000 (JP) ........................................ 2000-345824

(51) Int. Cl.[7] ............................................. C07C 409/20
(52) U.S. Cl. ....................................................... 568/567
(58) Field of Search ......................................... 568/567

(56) References Cited

FOREIGN PATENT DOCUMENTS

EP      0 990 631 A1     4/2000

Primary Examiner—Bernard Dentz
(74) Attorney, Agent, or Firm—Birch, Stewart, Kolasch & Birch, LLP

(57) ABSTRACT

A process of the invention allows a cycloalkane to react with oxygen in the presence of a catalytic imide compound having an N-hydroxy (or N-oxo) cyclic imide skeleton and thereby yields a corresponding bis(1-hydroxycycloalkyl) peroxide. The catalytic imide compound includes, for example, a compound represented by following Formula (1):

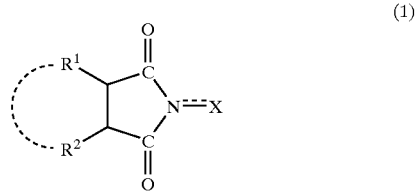

wherein $R^1$ and $R^2$ are each, for example, a hydrogen atom, a halogen atom, an alkyl group, an aryl group or a cycloalkyl group, where $R^1$ and $R^2$ may be combined to form a double bond, an aromatic or non-aromatic ring; and X is an oxygen atom or a hydroxyl group. The cycloalkane includes, for example, a cycloalkane having from 5 to 15 members. The invention can easily produce bis(1-hydroxycycloalkyl) peroxide from an inexpensive material.

3 Claims, No Drawings

PROCESS FOR PRODUCING ORGANIC PEROXIDES

This application is the national phase under 35 U.S.C. § 371 of PCT International Application No. PCT/JP01/09768 which has an International filing date of Nov. 8, 2001, which designated the United States of America.

TECHNICAL FIELD

The present invention relates to a process for producing bis(1-hydroxycycloalkyl) peroxides that are useful as, for example, raw materials for lactones and lactams.

BACKGROUND ART

Bis(1-hydroxycycloalkyl) peroxides are useful as, for example, raw materials for lactones and lactams. For example, By treating bis(1-hydroxycyclohexyl) peroxide with an acid, ε-caprolactone, which is important as a raw material for a polyester, can be produced in a good yield (U.S. Pat. No. 4,183,863). By allowing ammonia to act upon bis(1-hydroxycyclohexyl) peroxide, ε-caprolactam, which is useful as a raw material for a polyamide, can be obtained (Japanese Examined Patent Application Publication No. 46-25742).

Liebig Annalen der Chemie, vol. 565, pp. 7 (1949) discloses a process for producing a bis(1-hydroxycycloalkyl) peroxide by allowing cyclohexanone to react with hydrogen peroxide. This process, however, requires expensive hydrogen peroxide as a raw material and is not appropriate as an industrial process. PCT International Publication No. WO99/50204 mentions that, by allowing cyclohexanol to react with oxygen in the presence of cyclohexanone and N-hydroxyphthalimide and then allowing indium chloride to act upon the resulting mixture, bis(1-hydroxycyclohexyl) peroxide is produced in addition to ε-caprolactone. This process, however, requires relatively expensive cyclohexanol as a raw material, also requires cyclohexanone and is disadvantageous.

DISCLOSURE OF INVENTION

Accordingly, an object of the present invention is to provide a process for easily producing a bis(1-hydroxycycloalkyl) peroxide from an inexpensive raw material.

Another object of the present invention is to provide a process for directly producing a bis(1-hydroxycycloalkyl) peroxide from a cycloalkane and oxygen.

After intensive investigations to achieve the above objects, the present inventors have found that a bis(1-hydroxycycloalkyl) peroxide is directly produced from a cycloalkane and oxygen by using a specific catalyst. The present invention has been accomplished based on these findings.

Specifically, the present invention provides a process for producing an organic peroxide, the process including the step of allowing a cycloalkane to react with oxygen in the presence of a catalytic imide compound having an N-hydroxy (or N-oxo) cyclic imide skeleton to yield a corresponding bis(1-hydroxycycloalkyl) peroxide.

The catalytic imide compound includes, for example, a compound represented by following Formula (1):

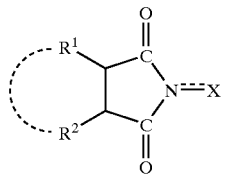

wherein $R^1$ and $R^2$ are the same or different and are each a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, an aromatic or non-aromatic ring; X is an oxygen atom or a hydroxyl group; and one or two of N-substituted cyclic imido group indicated in the formula may be further formed on the $R^1$, $R^2$, or on the double bond or aromatic or non-aromatic ring formed by $R^1$ and $R^2$. The cycloalkane includes, for example, cycloalkanes each having from 5 to 15 members.

BEST MODE FOR CARRYING OUT THE INVENTION

[Cycloalkanes]

Cycloalkanes for use as starting materials in the present, invention include, but are not limited to, cyclopropane, cyclobutane, cyclopentane, cyclohexane, cycloheptane, cyclooctane, cyclononane, cyclodecane, cyclododecane, cyclotetradecane, cyclohexandecane, cyclooctadecane, cycloicosane, cyclodocosane, cyclotriacontane, and other cycloalkanes each having from about 3 to about 30 members. Among them, cyclopentane, cyclohexane, cyclooctane, cyclododecane, and other cycloalkanes each having from about 5 to about 15 members are preferred, of which cyclohexane and cyclododecane are typically preferred.

These cycloalkanes may have at least one substituent within a range not adversely affecting a reaction. Such substituents include, but are not limited to, halogen atoms, oxo group, hydroxyl group, mercapto group, substituted oxy groups (e.g., alkoxy groups, aryloxy groups and acyloxy groups), substituted thio groups, carboxyl group, substituted oxycarbonyl groups, substituted or unsubstituted carbamoyl groups, cyano group, nitro group, substituted or unsubstituted amino groups, alkyl groups (e.g., methyl, ethyl, isopropyl, t-butyl, hexylk octyl, decyl, and other $C_1$–$C_{20}$ alkyl groups, of which $C_1$–$C_4$ alkyl groups are preferred), alkenyl groups, alkynyl groups, cycloalkyl groups, cycloalkenyl groups, aryl groups (e.g., phenyl and naphthyl groups), aralkyl groups (e.g., benzyl group), and heterocyclic groups. Each of the cycloalkanes may have an aromatic or non-aromatic carbon ring or heterocyclic ring condensed to the cycloalkane ring within a range not adversely affecting the reaction.

[Oxygen]

As oxygen, either of molecular oxygen and nascent oxygen can be used. The molecular oxygen is not specifically limited and includes pure oxygen, oxygen diluted with an inert gas such as nitrogen, helium, argon or carbon dioxide, and air. Oxygen can be formed in the reaction system. The amount of oxygen is generally equal to or more than about 0.5 mole (for example, equal to or more than about 1 mole), preferably from about 1 to about 100 moles, and more preferably from about 2 to about 50 moles, relative to 1 mole of the substrate cycloalkane. Oxygen is often used in excess moles to the substrate.

[Catalytic Imide Compounds]

According to the present invention, an imide compound having an N-hydroxy (or N-oxo) cyclic imide skeleton is used as a catalyst. Such imide compounds include, for example, the compounds represented by Formula (1).

Of the substituents $R^1$ and $R^2$ in the imide compounds represented by Formula (1), the halogen atom includes iodine, bromine, chlorine and fluorine atoms. The alkyl group includes, but is not limited to, methyl, ethyl, propyl, isopropyl, butyl, isobutyl, s-butyl, t-butyl, pentyl, hexyl, heptyl, octyl, decyl, and other straight- or branched-chain alkyl groups each having from about 1 to about 10 carbon atoms. Preferred alkyl groups are alkyl groups each having from about 1 to about 6 carbon atoms, of which lower alkyl groups each having from about 1 to about 4 carbon atoms are typically preferred.

The aryl group includes phenyl and naphthyl groups, for example. Illustrative cycloalkyl groups include cyclopentyl and cyclohexyl groups. Illustrative alkoxy groups are methoxy, ethoxy, propoxy, isopropoxy, butoxy, isobutoxy, t-butoxy, pentyloxy, hexyloxy, and other alkoxy groups each having from about 1 to about 10 carbon atoms, and preferably having from about 1 to about 6 carbon atoms. Among them, lower alkoxy groups each having from about 1 to about 4 carbon atoms are typically preferred.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having from about 1 to about 10 carbon atoms in the alkoxy moiety. Preferred alkoxycarbonyl groups are alkoxycarbonyl groups each having from about 1 to about 6 carbon atoms in the alkoxy moiety, of which lower alkoxycarbonyl groups each having from about 1 to about 4 carbon atoms in the alkoxy moiety are typically preferred.

The acyl group includes, but is not limited to, formyl, acetyl, propionyl, butyryl, isobutyryl, valeryl, isovaleryl, pivaloyl, and other acyl groups each having from about 1 to about 6 carbon atoms.

The substituents $R^1$ and $R^2$ may be identical to or different from each other. The substituents $R^1$ and $R^2$ in Formula (1) may be combined to form a double bond, or an aromatic or non-aromatic ring. The preferred aromatic or non-aromatic ring is a 5- to 12-membered ring, and especially a 6- to 10-membered ring. The ring may be a heterocyclic ring or condensed heterocyclic ring, but it is often a hydrocarbon ring. Such rings include, but are not limited to, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring is composed of an aromatic ring in many cases. The ring may have at least one substituent. Such substituents include, for example, alkyl groups, haloalkyl groups, hydroxyl group, alkoxy groups, carboxyl group, alkoxycarbonyl groups, acyl groups, nitro group, cyano group, amino groups, and halogen atoms.

In Formula (1), X represents an oxygen atom or a hydroxyl group, and the bond between the nitrogen atom N and X is a single bond or a double bond.

On $R^1$, $R^2$, or on the double bond or aromatic or non-aromatic ring formed by $R^1$ and $R^2$, one or two of the N-substituted cyclic imido group indicated in Formula (1) may be further formed. For example, when $R^1$ or $R^2$ is an alkyl group having two or more carbon atoms, the N-substituted cyclic imido group may be formed together with the adjacent two carbon atoms constituting the alkyl group. Likewise, when $R^1$ and $R^2$ are combined to form a double bond, the N-substituted cyclic imido group may be formed together with the double bond. when $R^1$ and $R^2$ are combined to form an aromatic or non-aromatic ring, the N-substituted cyclic imido group may be formed with the adjacent two carbon atoms constituting the ring.

Preferred imide compounds include compounds of the following formulae:

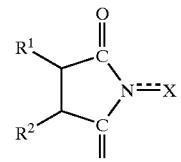

(1a)

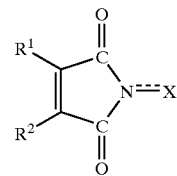

(1b)

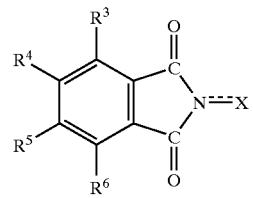

(1c)

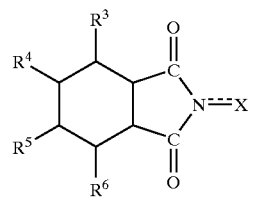

(1d)

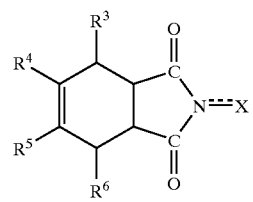

(1e)

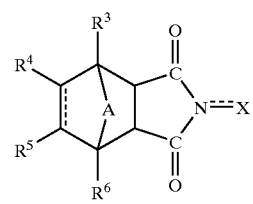

(1f)

wherein $R^3$ to $R^6$ are the same or different and are each a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where adjacent groups of $R^3$ to $R^6$ may be combined to form an aromatic or non-aromatic ring; A in Formula (1f) is a methylene group or an oxygen atom; and $R^1$, $R^2$ and X have the same meanings as defined above, where one or two of the N-substituted cyclic imido group indicated in Formula (1c) may be further formed on the benzene ring in Formula (1c).

In the substituents $R^3$ to $R^6$, the alkyl group includes similar alkyl groups to those exemplified above, of which alkyl groups each having from about 1 to about 6 carbon atoms are preferred. The haloalkyl group includes trifluoromethyl group and other haloalkyl groups each having from about 1 to about 4 carbon atoms. The alkoxy group includes similar alkoxy groups to those mentioned above, of which lower alkoxy groups each having from about 1 to about 4 carbon atoms are preferred. The alkoxycarbonyl group includes similar alkoxycarbonyl groups to those described above, of which lower alkoxycarbonyl groups each having from about 1 to about 4 carbon atoms in the alkoxy moiety are preferred. The acyl group includes similar acyl groups to those described above, of which acyl groups each having from about 1 to about 6 carbon atoms are preferred. The illustrative halogen atoms include fluorine, chlorine and bromine atoms. Each of the substituents $R^3$ to $R^6$ is often a hydrogen atom, a lower alkyl group having from about 1 to about 4 carbon atoms, a carboxyl group, a nitro group, or a halogen atom. The ring formed together by $R^3$ to $R^6$ includes similar rings to the aforementioned rings which are formed together by $R^1$ and $R^2$. Among them, aromatic or non-aromatic 5- to 12-membered rings are typically preferred.

Preferred imide compounds include, for example, N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds represented by Formula (1) can be prepared by a conventional imidization process (a process for the formation of an imide), such as a process in which a corresponding acid anhydride is allowed to react with hydroxylamine $NH_2OH$ for ring-opening of an acid anhydride group, and the ring is then closed to form an imide.

Such acid anhydrides include succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are especially preferred.

Each of the imide compounds having an N-hydroxy (or N-oxo) cyclic imide skeleton can be used alone or in combination. The imide compounds can be used as being supported by a carrier. As such carriers, activated carbon, zeolite, silica, silica-alumina, bentonite, and other porous carries are often employed. The amount of the imide compound on the carrier is, for example, from about 0.1 to about 50 parts by weight, preferably from about 0.5 to about 30 parts by weight, and more preferably from about 1 to about 20 parts by weight, relative to 100 parts by weight of the carrier.

The amount of the imide compound can be selected within a wide range and is, for example, from about 0.000001 to about 1 mole, preferably from about 0.00001 to about 0.5 mole, and more preferably from about 0.0001 to 0.4 mole, relative to 1 mole of the cycloalkane.

[Promoter (Co-catalyst)]

According to the invention, a promoter (co-catalyst) can be used in combination with the catalytic imide compound. Such promoters include, for example, metallic compounds. By using the imide compound in combination with the metallic compound, the rate and selectivity of the reaction can be improved.

Metallic elements constituting the metallic compounds are not specifically limited and are often metallic elements of the Groups 2 to 15 of the Periodic Table of Elements. The term "metallic element" as used herein also includes boron B. Examples of the metallic elements include, of the Periodic Table of Elements, Group 2 elements (e.g., Mg, Ca, Sr and Ba), Groups 3 elements (e.g., Sc, lanthanoid elements and actinoid elements), Group 4 elements (e.g., Ti, Zr and Hf), Group 5 elements (e.g., V), Group 6 elements (e.g., Cr, Mo and W), Group 7 elements (e.g., Mn), Group 8 elements (e.g., Fe and Ru), Group 9 elements (e.g., Co and Rh), Group 10 elements (e.g., Ni, Pd and Pt), Group 11 elements (e.g., Cu), Group 12 elements (e.g., Zn), Groups 13 elements (e.g., B, Al and In), Group 14 elements (e.g., Sn and Pb), and Group 15 elements (e.g., Sb and Bi). Preferred metallic elements include transition metal elements (elements of Groups 3 to 12 of the Periodic Table of Elements) and Group 13 elements of the Periodic Table of Elements. Among them, elements of the Groups 5 to 11 and Group 13 of the Periodic Table of Elements are preferred, of which elements of Groups 5 to 9 and Group 13 are typically preferred. Especially, V, Mo, Mn, Co and In are preferred, of which Mn, Co and In are typically preferred. The valency of the metallic element is not specifically limited and is from about 0 to about 6 in many cases.

Such metallic compounds include, but are not limited to, elementary substances, hydroxides, oxides (including complex oxides), halides (fluorides, chlorides, bromides and iodides), saltsofoxoacids (e.g., nitrates, sulfates, phosphates, borates, and carbonates), salts of isopoly acids, salts of heteropoly acids, and other inorganic compounds of the aforementioned metallic elements; salts of organic acids (e.g., acetates, propionates, prussiates, naphthenates and stearates), complexes, and other organic compounds of the metallic elements. Ligands for constituting the complexes include OH (hydroxo), alkoxy (e.g., methoxy, ethoxy, propoxy, and butoxy), acyl (e.g., acetyl and propionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphines (triphenylphosphine and other triarylphosphines) and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Specific examples of the metallic compounds include, by taking cobalt compounds as an example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; acetylacetonatocobalt and other complexes, and other divalent or trivalent cobalt compounds. Illustrative vanadium compounds include, but are not limited to, vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valence of from 2 to 5. Examples of compounds of the other metallic elements include compounds corresponding to the above-mentioned cobalt or vanadium compounds. Each of these metallic compounds can be used alone or in combination.

The amount of the metallic compound is, for example, from about 0.001 to about 0.1 mole, and preferably from about 0.005 to about 0.08 mole, relative to 1 mole of the imide compound.

The promoters for use in the present invention also include organic salts each comprising a polyatomic cation or a polyatomic anion and its counter ion, which polyatomic cation or anion contains a Group 15 or Group 16 element of the Periodic Table of Elements having at least one organic group combined therewith. By using the organic salts as the promoters, the rate and selectivity of the reaction can further be improved.

In the organic salts, the Group 15 elements of the Periodic Table of Elements include N, P, As, Sb, and Bi, and the Group 16 elements of the Periodic Table of Elements include, for example, O, S, Se and Te. Preferred elements are N, P, As, Sb and S, of which N, P and S are typically preferred.

The organic groups to be combined with atoms of the elements include, but are not limited to, hydrocarbon groups which may have a substituent, and substituted oxy groups. The hydrocarbon groups include, but are not limited to, methyl, ethyl, propyl, isopropyl, butyl, isobutyl, s-butyl, t-butyl, pentyl, hexyl, octyl, decyl, tetradecyl, hexadecyl, octadecyl, allyl, and other straight- or branched-chain aliphatic hydrocarbon groups (alkyl groups, alkenyl groups and alkynyl groups) each having from about 1 to about 30 carbon atoms (preferably from about 1 to about 20 carbon atoms); cyclopentyl, cyclohexyl, and other alicyclic hydrocarbon groups each having from about 3 to about 8 carbon atoms; and phenyl, naphthyl, and other aromatic hydrocarbon groups each having from about 6 to about 14 carbon atoms. Substituents which the hydrocarbon groups may have include, but are not limited to, halogen atoms, oxo group, hydroxyl group, substituted oxy groups (e.g., alkoxy groups, aryloxy groups, and acyloxy groups), carboxyl group, substituted oxycarbonyl groups, substituted or unsubstituted carbamoyl groups, cyano group, nitro group, substituted or unsubstituted amino groups, alkyl groups (e.g., methyl, ethyl, and other $C_1$–$C_4$ alkyl groups), cycloalkyl groups, aryl groups (e.g., phenyl and naphthyl groups), and heterocyclic groups. The preferred hydrocarbon groups include, for example, alkyl groups each having from about 1 to about 30 carbon atoms, and aromatic hydrocarbon groups (especially, phenyl or naphthyl group) each having from about 6 to about 14 carbon atoms. The substituted oxy groups include, but are not limited to, alkoxy groups, aryloxy groups and aralkyloxy groups.

Examples of the organic salts include organic ammonium salts, organic phosphonium salts, organic sulfonium salts, and other organic onium salts. Such organic ammonium salts include, for example, tetramethylammonium chloride, tetraethylarnmonium chloride, tetrabutylammonium chloride, tetrahexylammonium chloride, trioctylmethylammonium chloride, triethylphenylammonium chloride, tributyl(hexadecyl)ammonium chloride, di(octadecyl)dimethylammonium chloride, and other quaternary ammonium chlorides, and corresponding quaternary ammonium bromides, and other quaternary ammonium salts each having four hydrocarbon groups combined with a nitrogen atom; dimethylpiperidinium chloride, hexadecylpyridinium chloride, methylquinolinium chloride, and other cyclic quaternary ammonium salts. Examples of the organic phosphonium salts include tetramethylphosphonium chloride, tetrabutylphosphonium chloride, tributyl(hexadecyl)phosphonium chloride, triethylphenylphosphonium chloride, and other quaternary phosphonium chlorides, and corresponding quaternary phosphonium bromides, and other quaternary phosphonium salts each having four hydrocarbon groups combined with a phosphorus atom. Examples of the organic sulfonium salts include triethylsulfonium iodide, ethyldiphenylsulfonium iodide, and other sulfonium salts each having three hydrocarbon groups combined with a sulfur atom.

The organic salts also include methanesulfonates, ethanesulfonates, octanesulfonates, dodecanesulfonates, and other alkyl-substituted sulfonates (e.g., $C_6$–$C_{18}$ alkyl-substituted sulfonates); benzenesulfonates, p-toluenesulfonates, naphthalenesulfonates, decylbenzenesulfonates, dodecylbenzenesulfonates, and other aryl-substituted sulfonates which may be substituted with an alkyl group (e.g., $C_6$–$C_{18}$ alkyl-substituted arylsulfonates); sulfonic acid type ion exchange resins (ion exchangers); and phosphonic acid type ion exchange resins (ion exchangers).

The amount of the organic salt is, for example, from about 0.001 to about 0.1 mole and preferably from about 0.005 to about 0.08 mole, relative to 1 mole of the imide compound.

According to the process of the present invention, the reaction system may include a radical generator or a radical reaction accelerator. Such components include, but are not limited to, halogens (e.g., chlorine and bromine), peracids (e.g., peracetic acid and m-chloroperbenzoic acid), and peroxides (e.g., hydrogen peroxide, t-butyl hydroperoxide (TBHP), and other hydroperoxides). The system also include nitric acid, nitrous acid or a salt thereof. The existence of such a component in the system enhances a reaction in some cases. The amount of the aforementioned component is, for example, from about 0.001 to about 0.1 mole relative to 1 mole of the imide compound.

[Reaction]

The reaction can be performed in the presence of, or in the absence of, a solvent. Such solvents include, but are not limited to, benzene and other aromatic hydrocarbons; dichloromethane, chloroform, 1,2-dichloroethane, dichlorobenzene, and other halogenated hydrocarbons; t-butanol, t-amyl alcohol, and other alcohols; acetonitrile, benzonitrile, and other nitrites; acetic acid, propionic acid, and other organic acids; formamide, acetamide, dimethylformamide (DMF), dimethylacetamide, and other amides; and mixtures of these solvents.

A reaction temperature can be selected depending on, for example, the type of the reaction material within a range of, for example, from about 40° C. to about 200° C., preferably from about 60° C. to about 150° C., and more preferably from about 70° C. to about 100° C. The reaction can be performed at atmospheric pressure or under a pressure (under a load). The reaction-can be performed in the presence of, or under flow of, oxygen in a conventional system such as a batch system, semi-batch system or continuous system.

According to the present invention, a starting material cycloalkane represented by Formula (2) yields a corresponding bis(1-hydroxycycloalkyl) peroxide represented by Formula (3) as a result of a reaction in accordance with the following reaction process chart. For example, cyclohexane yields bis(1-hydroxycyclohexyl) peroxide, and cyclododecane yields bis(1-hydroxycyclododecyl) peroxide.

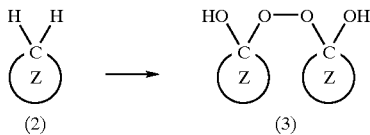

In the above formulae, ring Z is a cycloalkane ring.

After the completion of the reaction, reaction products can be separated and purified by a technique such as filtration, concentration, distillation, extraction, crystallization, recrystallization, adsorption, column chromatography and other separation means, or any combination of these separation means. For example, the product bis(1-hydroxycycloalkyl) peroxide can be isolated as a result of crystallization by adding a poor solvent such as methanol or cyclohexanone to the reaction mixture.

The product bis(1-hydroxycycloalkyl) peroxide can be quantitated by redox titration using, for example, iodometry. It can also be quantitated, for example, by high performance liquid chromatography.

INDUSTRIAL APPLICABILITY

The present invention can easily produce a bis(1-hydroxycycloalkyl) peroxide from an inexpensive raw material and can directly produce a bis(1-hydroxycycloalkyl) peroxide from a cycloalkane and oxygen.

EXAMPLES

The present invention will be illustrated in further detail with reference to an example below, which is not intended to limit the scope of the invention.

Example 1

In a 100-ml flask, 16.0 g (190 mmol) of cyclohexane, 3.1 g (19 mmol) of N-hydroxyphthalimide, 0.048 g (0.19 mmol) of cobalt(II) acetate tetrahydrate and 34.0 g of acetonitrile were placed and were allowed to react at 90° C. in an atmosphere of oxygen gas at atmospheric pressure for 1 hour with stirring. Reaction products were analyzed to find that bis(1-hydroxycyclohexyl) peroxide represented by following Formula (4) was produced in a yield of 20% on the basis of cyclohexane.

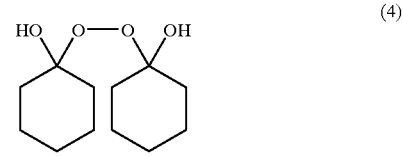

What is claimed is:

1. A process for producing an organic peroxide, the process comprising the step of allowing a cycloalkane to react with oxygen in the presence of a catalytic imide compound having an N-hydroxy (or N-oxo) cyclic imide skeleton to yield a corresponding bis(1-hydroxycycloalkyl) peroxide.

2. The process for producing an organic peroxide according to claim 1, wherein the catalytic imide compound is a compound represented by following Formula (1):

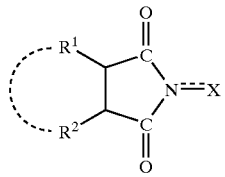

wherein $R^1$ and $R^2$ are the same or different and are each a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond or an aromatic or non-aromatic ring; X is an oxygen atom or a hydroxyl group; and one or two of N-substituted cyclic imido group indicated in the formula may be further formed on the $R^1$, $R^2$, or on the double bond or aromatic or non-aromatic ring formed by $R^1$ and $R^2$.

3. The process for producing an organic peroxide according to claim 1, wherein the cycloalkane is a cycloalkane having from 5 to 15 members.

* * * * *